US009731013B2

(12) United States Patent
Krishna et al.

(10) Patent No.: US 9,731,013 B2
(45) Date of Patent: Aug. 15, 2017

(54) DEVICES FOR THERMALLY INDUCED TRANSFORMATIONS CONTROLLED BY IRRADIATION OF FUNCTIONALIZED FULLERENES

(71) Applicant: UNIVERSITY OF FLORIDA RESEARCH FOUNDATION, INC., Gainesville, FL (US)

(72) Inventors: Vijay Krishna, Gainesville, FL (US); Karl R. Zawoy, High Springs, FL (US); Brij M. Moudgil, Gainesville, FL (US); Benjamin L. Koopman, Gainesville, FL (US); Nathanael Ian Stevens, Gainesville, FL (US); Kevin William Powers, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/666,803

(22) Filed: Mar. 24, 2015

(65) Prior Publication Data

US 2015/0190508 A1     Jul. 9, 2015

Related U.S. Application Data

(60) Division of application No. 13/106,355, filed on May 12, 2011, now Pat. No. 9,011,309, which is a continuation-in-part of application No. PCT/US2009/063719, filed on Nov. 9, 2009.

(60) Provisional application No. 61/113,698, filed on Nov. 12, 2008.

(51) Int. Cl.

| H01L 51/00 | (2006.01) |
| A61K 41/00 | (2006.01) |
| A61B 18/18 | (2006.01) |
| F42C 19/08 | (2006.01) |
| A61N 5/06 | (2006.01) |
| A61N 5/10 | (2006.01) |
| A61N 5/02 | (2006.01) |

(52) U.S. Cl.
CPC .......... *A61K 41/0052* (2013.01); *A61B 18/18* (2013.01); *A61B 18/1815* (2013.01); *A61N 5/062* (2013.01); *A61N 5/10* (2013.01); *F42C 19/08* (2013.01); *A61N 5/025* (2013.01); *A61N 5/0601* (2013.01); *A61N 2005/0659* (2013.01); *A61N 2005/0661* (2013.01); *A61N 2005/0662* (2013.01); *A61N 2005/1098* (2013.01); *Y10S 977/734* (2013.01); *Y10S 977/902* (2013.01); *Y10S 977/915* (2013.01); *Y10S 977/931* (2013.01)

(58) Field of Classification Search
None
See application file for complete search history.

(56) References Cited

U.S. PATENT DOCUMENTS

| 5,627,353 | A | 5/1997 | Oeste | |
| 5,994,410 | A | 11/1999 | Chiang et al. | |
| 6,864,503 | B2* | 3/2005 | Lung | H01L 45/06 257/246 |
| 2002/0169235 | A1 | 11/2002 | West et al. | |
| 2003/0118657 | A1 | 6/2003 | West et al. | |
| 2003/0156991 | A1 | 8/2003 | Halas et al. | |
| 2004/0197947 | A1* | 10/2004 | Fricke | G11C 13/0004 438/102 |
| 2005/0098204 | A1* | 5/2005 | Roscheisen | B82Y 10/00 136/263 |
| 2007/0249090 | A1* | 10/2007 | Philipp | H01L 45/06 438/102 |
| 2007/0282247 | A1 | 12/2007 | Desai et al. | |
| 2008/0096375 | A1* | 4/2008 | Chen | H01L 45/04 438/597 |
| 2008/0217445 | A1 | 9/2008 | Asahi et al. | |

FOREIGN PATENT DOCUMENTS

WO     WO 2008/140576 A2     11/2008

OTHER PUBLICATIONS

Velumani, Solar Energy Materials and Solar Cells, 76, 2003.*
Arayan, P.M. et al. "Nanotubes in a Flash—Ignition and Reconstruction" *Science*, Apr. 26, 2002, 296:705.
Dugan, L.L. et al. "Carboxyfullerenes as neuroprotective agents" *Proc. Natl. Acad. Sci. USA*, Aug. 1997, 94:9434-9439.
Mroz, P. et al. "Photodynamic therapy with fullerenes" *Photochem. Photobiol. Sci.*, 2007, 6:1139-1149.
Nakamura, E. et al. "Functionalized Fullerenes in Water. The First 10 Years of Their Chemistry, Biology, and Nanoscience" *Accounts of Chemical Research*, Nov. 2003, 36(11):807-815.
Sayes, C.M. et al. "Comparative Pulmonary Toxicity Assessments of $C_{60}$ Water Suspensions in Rats: Few Differences in Fullerene Toxicity in Vivo in Contrast to in Vitro Profiles" *Nano Lett.*, 2007, 7(8):2399-2406.
Trajković, S. et al. "Tissue-protective effects of fullerenol $C_{60}(OH)_{24}$ and amifostine in irradiated rats" *Colloids and Surfaces B: Biointerfaces*, 2007, 58:39-43.
Tseng, S.H. et al., "Ignition of carbon nanotubes using a photoflash," *Carbon*, 2007, pp. 958-964, vol. 45.
Hertel, I.V., et al., "Giant Plasmon Excitation in Free $C_{60}$ and $C_{70}$ Molecules Studied by Photoionization," *Physical Review Letters*, Feb. 10, 1992, pp. 784-787, vol. 68, No. 6.

\* cited by examiner

*Primary Examiner* — Susan Tran
*Assistant Examiner* — William Craigo
(74) *Attorney, Agent, or Firm* — Saliwanchik, Lloyd & Eisenschenk

(57) ABSTRACT

An electromagnetic radiation activated device comprises a property changing material and at least one functionalized fullerene that upon irradiation of the functionalized fullerenes with electromagnetic radiation of one or more frequencies a thermally activated chemical or physical transformation occurs in the property changing material. The thermal activated transformation of the property changing material is triggered by the heating or combustion of the functionalized fullerenes upon their irradiation. The device can include a chemical agent that is embedded in the property changing material and is released when the material is heated by the functionalized fullerenes upon irradiation.

2 Claims, 2 Drawing Sheets

DEVICES FOR THERMALLY INDUCED TRANSFORMATIONS CONTROLLED BY IRRADIATION OF FUNCTIONALIZED FULLERENES

CROSS-REFERENCE TO RELATED APPLICATIONS

This application is a divisional of U.S. patent application Ser. No. 13/106,355, filed May 12, 2011, which is a continuation-in-part of International Patent Application No. PCT/US2009/063719, filed Nov. 9, 2009, which claims the benefit of U.S. Provisional Patent Application Ser. No. 61/113,698, filed Nov. 12, 2008, the disclosures of which are hereby incorporated by reference in their entireties, including all figures, tables or drawings.

BACKGROUND OF THE INVENTION

Many processes require an initiation stimulus to start a reaction by releasing heat, and a device to achieve this goal is a critical system component for many processes, such as combustion processes. For combustion processes many different ignition methods exist, the most popular being an electric spark igniter. However, spark igniters require high-energy input supplied by a high-voltage circuitry and by its nature is a single-point stimulus method. Other ignition methods, such as plasma jet injection or flame jet initiation and high-power laser ignition, are all bulky, heavy, and expensive to operate.

There have been some recent reports of optical ignition of carbon nanotubes in oxidizing ambient gases, such as in air. For example, researchers have reported that single-walled carbon nanotubes ignite when exposed to a conventional photographic flash (Ajayan et al., "Nanotubes in a Flash-Ignition and Reconstruction", *Science*, Vol. 296, Apr. 26, 2002). This photoeffect is disclosed to occur for single-walled carbon nanotubes prepared by carbon arc, laser ablation, or chemical vapor deposition techniques upon exposure to a camera flash at close range. Ignition and burning is reported to occur when local increases in temperature are sufficient to initiate the oxidation of the carbon and propagate as more heat is released by the exothermic reaction. Heat confinement in nanostructures can thus lead to drastic structural reformation and, under oxidizing environments, induce ignition under conditions not expected for bulk materials. The heat pulse is created by light absorption by the nanotubes from a proximal light flash.

Applications of optical heating or ignition of carbon nanotubes are limited by several characteristics of carbon nanotubes that include size, high aspect ratio, insolubility in water or other liquids, and lack of biocompatibility. Compositions are needed that provide radiation induced heating or ignition in water or other liquids as well as air, have small size and low aspect ratio, and are miscible in a host of materials such that the properties of the materials can be altered by thermal transitions that are promoted photochemically. Moreover, compositions that are biocompatible would allow their use in medical applications.

BRIEF SUMMARY OF THE INVENTION

Embodiments of the invention are directed to an electromagnetic radiation activated device where a property changing material that can undergo thermally activated chemical or physical transformation is coupled with at least one functionalized fullerene that heat or combust when irradiated with electromagnetic radiation of one or more frequencies to thermally activate the transformation of the property changing material. Radio wave, microwave, infrared, near infrared, visible, ultraviolet, extreme ultraviolet, x-ray, and/or gamma ray of any single or combination of frequencies can be employed for the irradiation of the functionalized fullerenes. Coherent or incoherent electromagnetic radiation sources can be employed. Functionalized fullerenes that can be used in devices include polyhydroxyl fullerene derivatives (PHFs), carboxy fullerenes, N-ethyl-polyamino-$C_{60}$s, [6,6] phenyl $C_{60}$ butyric acid methyl esters (PCBMs), fullerene hydrides, N-methyl fulleropyrrolidine, or combinations thereof. These functionalized fullerenes can be restricted to a surface of the property changing material or can be distributed through at least a portion of the property change material.

In one embodiment of the invention, property changing materials can be transformed or switched between a plurality of physical states, each having a different discernable degree of crystallinity. In one embodiment the property changing material comprises a germanium, antimony tellurium chalcogenide alloy (GST) for devices that can be employed as phase change random access memory (PRAM) chips or RW compact disc (CD) or digital video disc (DVD) optical storage memory devices.

In some embodiments of the invention the property changing material can be a plastic, such as polyethylene or polypropylene where the physical transformation can be melting and solidification of the plastic by the radiation induced heating of the functionalized fullerenes in contact with the plastic. The functionalized fullerenes can be contained in a tape of the plastic attached as a portion of a device where the remainder of the device is constructed of the plastic free of functionalized fullerenes. The device can be used for sealing or opening of a container upon irradiation.

In some embodiments of the invention a chemical agent can be included. The chemical agent can be encapsulated by the property changing material where the chemical agent is released upon irradiation of the functionalized fullerenes where the property changing material is activated thermally in the vicinity of the functionalized fullerenes to enhance diffusion of the chemical agent in the property changing material. Devices for biomedical applications can employ property changing material that are or are derived from poly(lactic-co-glycolic acid) (PLGA), poly(ethylene glycol) (PEG), or chitosan to render the materials biocompatible. The chemical agent can be drugs, nutraceuticals, proteins, hormones, or a combination of these agents. For example, the device can function as a light activated transdermal patch or an implant to deliver chemical agent such as nicotine, insulin, estrogen, contraceptives, pain killers, antidepressants or other drug.

In one embodiment the chemical agent can be a drug that promotes coagulation. The device can be delivered to an aneurysm where the drug can be released upon irradiation to promote clotting in the aneurysm. In another embodiment the property changing material can be a polymeric coating on a stent where the chemical agent is an immunosuppressive drug dispersed in the coating for release upon irradiation. In another embodiment the property changing material is a polymer coated upon seeds or a particle dispersed with seeds where hormones, insecticides, herbicides, fertilizers or minerals are included as chemical agents within the coating or particles to promote uniform germination of the seeds after irradiation of the functionalized fullerenes.

In another embodiment, the property changing material can be one or more thermally activated dyes absorbed on paper or within a polymeric coating on paper. Upon irradiation, the functionalized fullerenes promote a color change in the dyes that are heated in the vicinity of the functionalized fullerenes such that images or text can be formed on the paper. The color and opacity of the dyes can be modified after printing through the application irradiation induced thermal energy.

In another embodiment of the invention a method of destroying tumors involves providing a plurality of functionalized fullerenes conjugated with a tumor targeting agent, delivering the functionalized fullerenes to an organism having at least one tumor, and irradiating the functionalized fullerenes with radio waves such that the functionalized fullerenes that have targeted the tumors heat and destroy the tumors.

In another embodiment of the invention, a method for detonating an explosion involves providing a plurality of functionalized fullerenes on or in at least a portion of an explosive material and irradiating the functionalized fullerenes with electromagnetic radiation to ignite the functionalized fullerenes to cause the detonation of the explosive material. The irradiation source can be attached to the explosive device or can be remote to the device. The explosive devices can be employed for defense, demolition, construction, mining or firework applications.

DETAILED DESCRIPTION OF THE INVENTION

Figure 1:
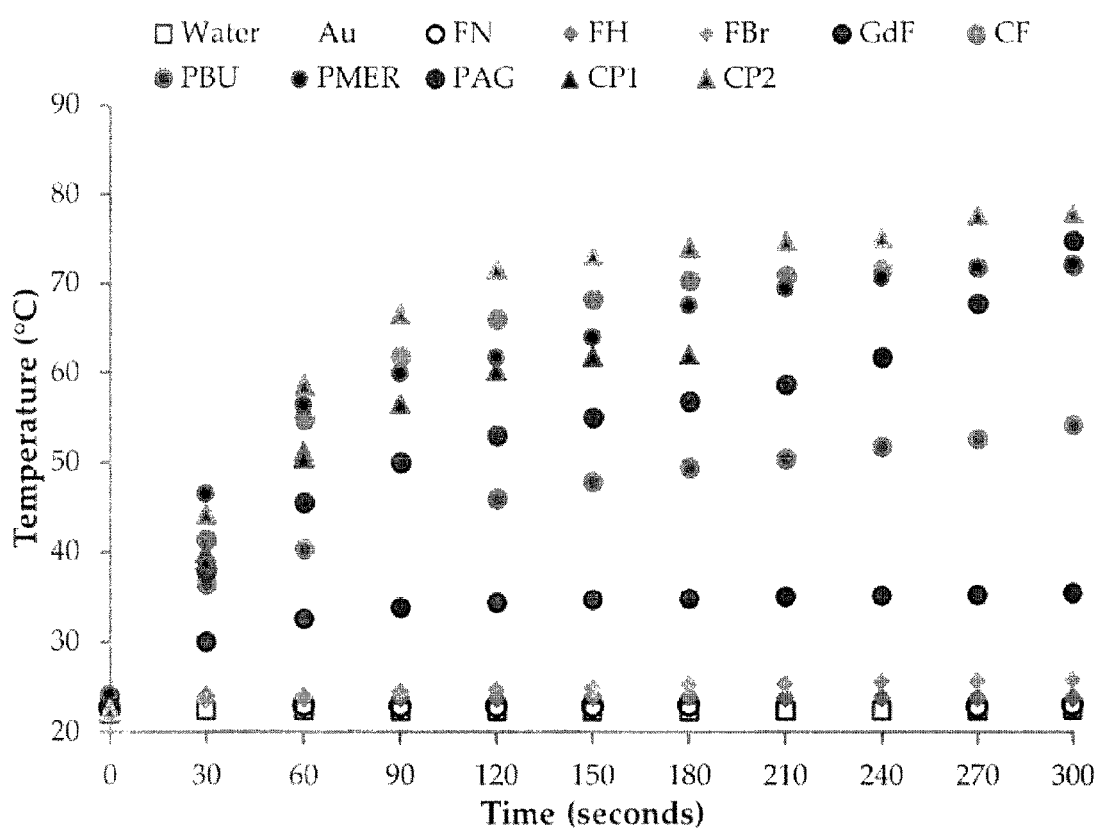
FIG. 1 is a plot of the temperature rise of samples comprising functionalized fullerenes according to embodiments of the invention that are dissolved or suspended in water during irradiation with RF at 13.56 MHz and 500 W RF power over a period of five minutes.

Embodiments of the invention are directed to a property changing material that can undergo a thermally induced chemical reaction, a shift in a chemical equilibrium, a physical phase transition, or a change in degree of a physical property with temperature that is photoactivated by irradiation with a sufficient intensity of electromagnetic radiation due to the inclusion of functionalized fullerenes in the property changing material that heat upon absorption of the radiation. In some embodiments the thermally induced transition can be a chemical reaction that changes a few bonds within the property changing material without altering the chemical nature of the majority of the material, for example where cross-linking is destroyed by a thermal reaction. Physical property transitions that can be exploited according to embodiments of the invention include, but are not exclusive to melting, crystallizing, solubilizing, glass transitions, liquid crystalline transformations, and miscibility of blended material or block copolymer phases.

The functionalized fullerenes are irradiated with electromagnetic radiation having a wavelength and intensity sufficient to heat or even combust the functionalized fullerenes. Functionalized fullerenes can be included by disposing the particles on or within the material that undergoes thermally induced property changes. For example, in some embodiments of the invention, the functionalized fullerenes can be randomly or periodically dispersed through out a property changing material that is to be modified. In other embodiments of the invention, the functionalized fullerenes are restricted to a specific region of a structure of the material to be modified. In other embodiments of the invention, the functionalized fullerenes can be randomly or periodically disposed on a surface of the material to be modified. In some embodiments of the invention, one or more selected portions of the surface can be decorated with the functionalized fullerenes.

As has been recently discovered, Krishna et al., PCT/US2007/084956, filed Nov. 16, 2007, incorporated herein in its entirety, functionalized fullerenes heat, ignite or combust without the need for a spark, flame or other conventional initiator to produce significant local heating when irradiated by a suitable source. Heating or ignition can occur in a gaseous, liquid, or solid environment. A bright flash of visible light can be observed before combustion and, in some embodiments of the invention where oxygen in the vicinity of the functionalized fullerenes is controlled, the functionalized fullerenes can be used for devices that exploit the observed luminescence.

Suitable irradiation sources are those which provide sufficient energy for the desired degree of heating, lamination or combustion. The electronic states and transitions of fullerenes are near the interface between discrete molecular orbitals and band structures due to the large number of electrons in π orbitals. Because many electronic transitions are accessible, embodiments of the present invention can use many different wavelengths of the electromagnetic spectrum for excitation of the functionalized fullerenes. Hence, excitation can occur with the absorption of a sufficiently intense source of radiation in a wavelength range of about $10^3$ to about $10^{-12}$ m, encompassing radio wave, microwave, IR, Visible, UV, X-ray, and gamma ray irradiation.

Fullerenes are generally in the form of a spheroidal carbon comprising structure and are thus distinct from carbon nanotubes, which are essentially tubes with graphene surfaces. In contrast to the surface of carbon nanotubes, fullerenes have both five carbon and six carbon ring structures. Carbon nanotubes and fullerenes are physically and chemically stable molecules. Unlike carbon nanotubes and fullerenes, functionalized fullerenes are known to be biocompatible and can have therapeutic properties.

The term "fullerenes" defines a general class of molecules that exists essentially in the shape of a three dimensional polyhedron containing from 20 to 1500 carbon atoms, and which comprises carbon atoms as the predominant atomic moiety from which they are composed. The fullerene comprising molecules include but are not limited to fullerenes such as C-28, C-32, C-44, C-50, C-58, C-60, C-70, C-84, C-94, C-250 and C-540. According to this nomenclature, a fullerene containing 60 carbon atoms is denoted C-60 and a fullerene containing 70 carbon atoms is denoted C-70. The functionalized fullerenes for purposes of the invention are substituted fullerenes. These are molecular fullerenes which have one or more functional groups bound to the fullerene cage via covalent bonds, ionic bonds, Dewar bonds, Kubas interactions, or mixtures of these bonds. Functionalized fullerenes have side groups attached to the polyhedron. The side groups can be either inorganic, including but not exclusive to —OH, —Br, —H, —Ti, or organic, including but not exclusive to —C(COOH)$_2$ or combinations of organic and/or inorganic side groups. The number of side groups attached per cage of fullerene can vary from 1 to a majority of the number of carbons in the fullerene cage. Functionalized fullerenes have different physical and chemical properties based on the type and number of side groups. The functionalized fullerenes have dimensions that can be in excess of a nanometer in diameter, and can be considered nanoparticles.

Polyhydroxy fullerene derivatives (PHF), for example $C-60(OH)_n$ (n=1-48), also referred to as fullerols or fullerenols, can be used in embodiments of the invention. The number of —OH groups, n, is typically between 1 and 48. Polyhydroxy fullerene derivatives can be further derivatized to form other functionalized fullerenes according to embodiments of the invention. For example, the OH group can be converted into ethers or esters to yield functionalized fullerenes with enhanced miscibility in aqueous or non-aqueous environments.

In some embodiments of the invention, carboxy fullerenes, for example formula $C_{60}(C(COOH)_2)_3$, are water soluble and are reported to have therapeutic properties by Dugan et al. (*Proc. Natl Acad. Sci.*, 1997 Vol 94, 9434-9439). Carboxy fullerenes can be further derivatized, for example by esterification or amidation reactions, to form other functionalized fullerenes for use in various embodiments of the invention.

Other exemplary functionalized fullerenes include N-ethyl-polyamino-$C_{60}$, [6,6] phenyl $C_{60}$ butyric acid methyl ester (PCBM), fullerene hydride and N-methyl fulleropyrrolidine. Certain polymer chains can also be used as functional groups.

In one embodiment of the invention, functionalized fullerenes are disposed as a layer on a property changing material that can be rapidly switched between two or more states, for example, a germanium, antimony tellurium chalcogenide alloy (GST). The property changing material can be addressed by a laser beam. The energy from the laser beam causes the functionalized fullerenes to generate heat that causes the material to cycle between at least one phase to at least one other phase, which in the limit can be two phases, one being primarily crystalline and another primarily amorphous. The process of switching from one phase to another can occur rapidly, in about 5 nanoseconds or less. When the irradiation with electromagnetic radiation is of sufficient energy and maintained for a sufficient period of time, heating of a crystalline GST occurs to a temperature that causes melting of crystals, which upon cessation of the irradiation cools rapidly to a temperature below the crystallization temperature and traps the site in an amorphous state that has high electrical resistivity and a first refractive index and/or reflectivity. This amorphous material can then be irradiated with the same or another source of electromagnetic radiation, at the same or a different wavelength, for an appropriate period of time to promote heating to a temperature that is above the crystallization temperature yet below the melting point, such that the property changing material achieves a crystalline state that has a low resistivity and a second refractive index and/or reflectivity. Because of these differences in resistivity and refractive index for the different phases, the property changing material that is decorated with functionalized fullerenes can be used as phase change random access memory (PRAM) chip or RW compact disc (CD) or digital video disc (DVD) optical storage memory device.

The cycling between the two states can be carried out with a light source that is external to the PRAM chip, CD or DVD. The device can be constructed to be small in footprint, simple in design and low in power consumption. In other embodiments of the invention, the GST can be irradiated in a manner where one or more additional phases that are less than maximally amorphous or maximally crystalline are achieved. In these embodiments of the invention, one or more irradiation protocols that do not result in a fully amorphous or fully crystalline state are carried out to achieve one or more states with desired degrees of crystallization. For example, irradiating an amorphous state at a specific frequency, intensity and time allows the achievement of a specific temperature for a specific period of time that results in a specific partially crystalline GST with a resistivity and refractive index that is discernibly different than that of the maximally amorphous, maximally crystalline or other discernable partially crystalline states. In this manner, a chip or optical storage memory device can be constructed where every site on the device can switch between three or more states, allowing a dramatically larger information density than a device that has sites that switch between two states. If necessary, an optical storage memory device can be irradiated from one face where the functionalized fullerenes are addressed to generate the phase change, and be irradiated from another side to read the information from the property changing material such that the property changing material blocks any electromagnetic radiation that would excite the functionalized fullerenes and modify the information encoded in the property changing material in an undesired manner. The surface of the functionalized fullerene layer counter the property changing material can be coated with a material that acts as an oxygen barrier but is transparent to the electromagnetic radiation required for switching between states.

In other embodiments of the invention, a property changing material that comprises a plastic can have a dispersion of functionalized fullerenes within or on the surface of the plastic. Common thermoplastics, including, but not exclusive to, polyethylene and polypropylene can be used. In this manner, a container can be constructed to allow sealing upon irradiating the functionalized fullerenes of the property change material. In one embodiment of the invention, the functionalized fullerenes can be dispersed in or on a particular portion of the container and in another embodiment the functionalized fullerenes can be dispersed throughout the plastic of the entire container. The container can be sealed completely when the property changing material melts and resolidifies. In one embodiment the functionalized fullerenes can be in a tape in the proximity to the opening of the container such that the tape can be irradiated with a hand held irradiation source, such as a laser pen, an IR wand or other lamp to soften or melt the property change material. The container employing the tape need not be a single piece, but can consist of a body and a lid where the tape is placed between the body of the container and the lid to produce a seal. In another embodiment of the invention where the functionalized fullerenes are dispersed throughout plastic that comprises the container, irradiation of the functionalized fullerenes can soften or melt the entire container such that it can conform to the surface of a solid item to be packaged. A partial or complete vacuum can be imposed within the container such that the sealing can be induced to make intimate or nearly intimate contact between the item and container.

In embodiments of the invention, the property changing material is a polymeric material or other material that includes functionalized fullerenes and acts as an encapsulant. The functionalized fullerenes promote a change in the permeability of the material to an encapsulated chemical agent upon irradiation. In various embodiments of the invention, the encapsulated chemical agents can be drugs, nutraceuticals, proteins, hormones, or other natural products that may be of therapeutic value and the polymeric material can be a common drug delivery vehicle, such as PLGA, PEG, chitosan, or dendrimers, or can be a polymeric material specifically designed for a specific chemical agent, such as a functional polymer, block copolymer, network or dendrimer. Any mode by which permeability can be thermally changed can be employed. For example, the permeability can be enhanced for release on demand by having a thermally labile cross-link or other chain-link element within the polymeric material, such that it is rendered a poorer barrier to diffusion upon irradiation due to the degradation of bonds within the resin. Where these chain-link elements can exist in two different states (a bound state and an unbound state) depending upon temperature, the proportion of the elements in the two states can be photochemically biased that upon excitation of the functionalized fullerenes release is enabled. In one embodiment of the invention, the property changing material can be switched to render the encapsulants water soluble, water swellable or increase the encapsulants swellability and permeability upon irradiation. The encapsulants can comprise a non-property changing material that has a property changing material dispersed or bonded to it. For example, a property changing material in the form of small micro or nanoparticle, such as spheres or cylindrical rods, can be dispersed in a continuous phase that will not undergo a significant phase change thermally, such that the particles are rendered water soluble or swellable upon irradiation and form effective pores through which the encapsulated molecule can diffuse.

In one embodiment of the invention, the property changing material and functionalized fullerene comprising encapsulant can be employed as a transdermal patch for an encapsulated chemical agent. Such transdermal patches can be employed for the release of nicotine, insulin, estrogen, contraceptives, pain killers, antidepressants or any other drug or chemical agent that can be delivered through the skin. The rate of drug release can be controlled by the intensity and frequency of electromagnetic radiation delivered to the patch. For example, as the concentration of the chemical agent decreases within the patch, the rate of delivery for a given state of the property changing material will decrease. In one embodiment of the invention, upon irradiation of the property change material the permeability can be increased to compensate for the decrease in concentration such that a more constant rate of release can be achieved over the effective lifetime of the patch. In another embodiment of the invention, the property changing material is only permeable when under irradiation, and dosing can be carried out on demand by exposure of the patch to electromagnetic radiation.

In another embodiment of the invention, the property changing material can be employed as a subcutaneous delivery vehicle for a chemical agent. In this manner, an implant comprising the chemical agent encapsulated in the property changing material with functionalized fullerenes can be activated upon irradiation with electromagnetic radiation other than infrared to promote diffusion of the chemical agent from the implant by allowing selective heating of the implant without significantly heating the tissue around the implant, as occurs by infrared heating.

In another embodiment of the invention, the property changing material encapsulated chemical agent comprises a polymeric gel containing drugs and functionalized fullerenes. Blood cells can be encapsulated with the drug if desired. This gel material can be delivered via a catheter or needle to an aneurysm for uses as an alternative treatment to surgical clipping or endovascular coiling. After the gel material has been delivered to the aneurysm, irradiation can be used to release the drug and promote coagulation of blood, forming a clot that effectively eliminates the aneurysm.

In another embodiment of the invention, the property changing material comprises a polymeric coating with included functionalized fullerenes as a coating on a stent. The coating contains a drug that can be released when irradiated to enhance the diffusivity of the immunosuppressive drug through the coating. As desired, the drug can be released from the coating by irradiation such that restenosis of a blood vessel in the vicinity of a stent can be inhibited.

In an embodiment of the invention, the chemical agent encapsulated in a property changing material including functionalized fullerenes can be employed for agricultural uses. In one embodiment, seeds can be coated with an encapsulated chemical agent comprising one or more hormones that breaks down dormancy or promotes germination, insecticides, herbicides, fertilizers, minerals or other agents. In one embodiment of the invention, water or aqueous solutions can be encapsulated. In other embodiments of the invention, seeds can be packaged with dispersed particles of the encapsulated chemical agents or the encapsulated chemical agents can be dispersed over soil where seeds have been freshly planted. In this manner, a more uniform germination of a crop can be induced by irradiation due to the release of encapsulated chemical agents because the permeability of the property changing material has been increased thermally. In this manner, higher quantities and qualities of crops can be achieved.

In other embodiments of the invention, property change materials are used with functionalized fullerenes that are applied in a coating on paper. The property changing materials are one or more heat sensitive inks that reside in the coating or are absorbed on the paper under the coating. A scanning of the coating by a laser beam causes transformation of one or more essentially colorless inks into colored inks on the portions of the paper surface that are irradiated to form the image, for example text, on the paper. Alternately, light can be transmitted through a mask to generate the image without scanning.

In another embodiment of the invention, the property changing materials are individually encapsulated cyan, magenta, and yellow inks where different functionalized fullerenes reside with specific inks within the encapsulating material. A device can be constructed where these encapsulated dyes and functionalized fullerenes are dispersed on a surface which can be used as a reversible paper. Colored Inks could be designed to form a color by photolytic transformation and to bleach by a thermal transformation or vice versa. Hence by addressing a selected site on the surface with the appropriate frequency and intensity to selectively photolytically excite one state of an ink or photolytically excite its associated functionalized fullerene a specific color is either turned on or off at that site. By addressing multiple sites on the paper with different frequencies, desired images can be constructed or erased. The sites can be addressed by scanning with one or more lasers or projecting all different frequencies from a single source. The irradiation source can be in the form of an "electronic pencil" for manual imaging or can be a table, electronic tablet or printer built into a laptop computer upon which the device having a surface, such as a sheet of "electronic paper" can be laid or inserted. The printing head could operate similar to a scanner and fax when the paper is scanned then imprinted with an image in one pass through the printer. The printer could also be capable of printing an image on both sides of the electronic paper at one time.

In another embodiment of the invention functionalized fullerenes are conjugated with a tumor targeting agent. The functionalized fullerenes, for example, polyhydroxy fullerenes (PHF), can be irradiated with radio waves to generate heat or ignite to destroy the tumor cells by hyperthermia. Functionalized fullerenes can be circulated through the body until naturally expelled, as PHFs and some other functionalized fullerenes are not toxic.

Functionalized fullerenes can be ignited with light or even radio waves. In various embodiments of the invention, functionalized fullerenes can be included with a phase change material that comprises an exploding charge. This can allow the remote activation of the charge upon irradiation. The phase change material is the explosive which contains functionalized fullerenes at a specific site on the explosive material or dispersed throughout the material. A laser beam can be focused on a site with the functionalized fullerenes or scanned over the surface of the material to initiate the decomposition of the explosive material. In one embodiment of the invention, the materials can be used in a weapon or other device for defense applications or can be used in construction, demolition, mining or fireworks where detonation can be carried out on demand from a safe remote location when a light is directed on the functionalized fullerenes. The laser source can be remote or attached to the detonating charge and can be remote to or in the presence of the individual who controls the initiation of the explosion.

METHODS AND MATERIALS

Experimental Setup

Heating of a volume of water by irradiation of fullerene comprising compounds was carried out using a radiofrequency (RF) heating system (Therm Med, LLC, Erie, Pa.) operating at 13.56 MHz and 500 W RF power. A volume of 250 μL of sample dissolved or suspended in water was pipetted into a cylindrical quartz cuvette for RF exposure. The cuvette was placed on a thin horizontal Teflon sample holder positioned at a depth of 7.6 cm from RF generator.

Figure 2:
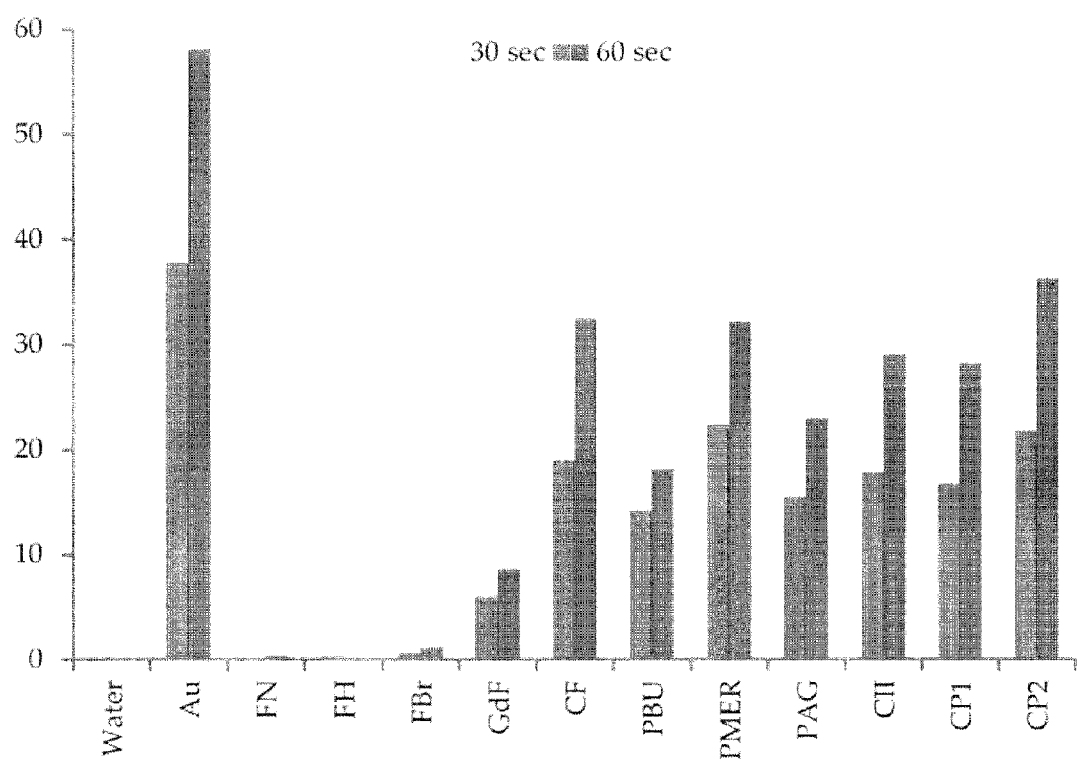
FIG. 2 is a bar graph of the temperature rise of samples comprising functionalized fullerenes according to embodiments of the invention that are dissolved or suspended in water after irradiation with RF at 13.56 MHz and 500 W RF power for 30 seconds (left bars) and 60 seconds (right bars).

Samples Tested
Water Millipore Water (Blank)
Au 5 nm gold nanoparticles (Control)
FN Pristine $C_{60}$ dispersed in Millipore water
FH Fullerene hydride dispersed in Millipore water
FBr Fullerene bromide dispersed in Millipore water
GdF Gadofullerene dispersed in Millipore water
CF Carboxy fullerene solution
PBU Polyhydroxy fullerenes purchased from BuckyUSA
PMER Polyhydroxy fullerenes synthesized at PERC
PAG Polyhydroxy fullerenes synthesized at PERC
CP1 PBU nanoparticles
CP2 PAG nanoparticles
CII Chitosan solution in 1% acetic acid
Results
As can be seen in FIGS. 1 and 2:
Water: No temperature rise is observed.
Gold: Gold nanoparticles exhibit a temperature rise of 58° C. in one minute.
FN: Pristine fullerenes did not show a temperature rise, which is consistent with observations with laser irradiation. Pristine fullerenes are not water soluble and float on the water surface.
FH: Fullerene hydride did not show a temperature rise, which is consistent with observations with laser irradiation. Fullerene hydride is not water soluble and float on the water surface.
FBr: Fullerene bromide did not show a temperature rise, which is consistent with observations with laser irradiation. Fullerene bromide is not water soluble and float on the water surface.
GdF: Gadofullerenes ($Gd@C_{82}$) exhibited a temperature rise of 10° C. in 5 minutes. Gadofullerenes are not water soluble and float on the water surface.
CF: Carboxy fullerene solution heated the solution to 55° C. in one minute ($\Delta T=32.4°$ C.) and 72° C. in 5 minutes.
PBU, PMER and PAG: Temperature rise was observed with polyhydroxy fullerenes solutions. The heating rate depended on the type of polyhydroxy fullerene with the highest temperature rise of 32° C. in one minute.
CP1 and CP2: Polyhydroxy fullerenes in nanoparticulate form exhibit a higher temperature rise than in solution. Temperature rise with CP2 was 36° C. in one minute.
CII: A temperature rise of 29° C. in one minute was observed for a chitosan solution that does not heat under laser irradiation.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An electromagnetic radiation activated memory device comprising:
a property changing material; and
at least one functionalized fullerene selected from the group consisting of polyhydroxy fullerene derivatives (PHFs), N ethyl-polyamino-$C_{60}$s, fullerene hydrides, N-methyl fulleropyrrolidine, or combinations thereof, wherein the functionalized fullerene is on a surface of the property changing material or is distributed through at least a portion of the property change material, wherein irradiation of said functionalized fullerene with electromagnetic radiation of one or more frequencies generates heat, and wherein said heat is transferred to said property changing material, which transforms between an amorphous and a crystalline state upon heating, wherein said property changing material comprises a germanium antimony tellurium chaleofzenide alloy (GST).

2. The device of claim 1, wherein said electromagnetic radiation activated memory device is a phase change random access memory (PRAM) chip, a RW compact disc (CD), or a digital video disc (DVD) optical storage memory device.

* * * * *